US012721296B2

(12) United States Patent
Kawashima

(10) Patent No.: US 12,721,296 B2
(45) Date of Patent: Sep. 1, 2026

(54) PETUNIA-CALIBRACHOA VARIETY SAKPXC038

(71) Applicant: Sakata Seed Corporation, Yokohama (JP)

(72) Inventor: Moriya Kawashima, Hamamatsu (JP)

(73) Assignee: Sakata Seed Corporation, Yokohama (JP)

( * ) Notice: Subject to any disclaimer, the term of this patent is extended or adjusted under 35 U.S.C. 154(b) by 109 days.

(21) Appl. No.: 18/786,517

(22) Filed: Jul. 28, 2024

(65) Prior Publication Data

US 2026/0026456 A1 Jan. 29, 2026

(51) Int. Cl.

| | |
|---|---|
| ***A01H 6/82*** | (2018.01) |
| ***A01H 1/00*** | (2006.01) |
| ***A01H 1/02*** | (2006.01) |
| ***A01H 4/00*** | (2006.01) |
| ***C12Q 1/6895*** | (2018.01) |

(52) U.S. Cl.

CPC ............ *A01H 6/824* (2018.05); *A01H 1/021* (2021.01); *A01H 1/123* (2021.01); *A01H 1/127* (2021.01); *A01H 4/005* (2013.01); *A01H 4/008* (2013.01); *A01H 6/821* (2018.05); *C12Q 1/6895* (2013.01)

(58) Field of Classification Search

None

See application file for complete search history.

(56) References Cited

U.S. PATENT DOCUMENTS

| | | | | |
|---|---|---|---|---|
| 10,492,458 | B2 | 12/2019 | Tsukahara | |
| 10,499,606 | B2 * | 12/2019 | Tsukahara .............. | A01H 6/824 |
| 11,871,718 | B1 * | 1/2024 | Kawashima ........... | A01H 6/821 |

* cited by examiner

*Primary Examiner* — Amjad Abraham

*Assistant Examiner* — Brian James Sullivan

(74) *Attorney, Agent, or Firm* — Weatherly IP Solutions, LLC; James M. Weatherly; Karen P. Bechtold

(57) ABSTRACT

A *Petunia-Calibrachoa* plant designated SAKPXC038 is disclosed. Embodiments include the seeds of *Petunia-Calibrachoa* SAKPXC038, the plants of *Petunia-Calibrachoa* SAKPXC038, to plant parts of *Petunia-Calibrachoa* SAKPXC038, and methods for producing a plant produced by crossing *Petunia-Calibrachoa* SAKPXC038 with itself or with another variety. Embodiments include methods for producing a plant containing in its genetic material one or more genes or transgenes and the transgenic plants and plant parts produced by those methods. Embodiments also relate to varieties, breeding varieties, plant parts, and cells derived from *Petunia-Calibrachoa* SAKPXC038, methods for producing other lines or plant parts derived from *Petunia-Calibrachoa* SAKPXC038, and the plants, varieties, and their parts derived from use of those methods. Embodiments further include hybrid seeds, plants, and plant parts produced by crossing *Petunia-Calibrachoa* SAKPXC038 with another variety.

19 Claims, No Drawings

PETUNIA-CALIBRACHOA VARIETY SAKPXC038

BACKGROUND

The embodiments recited herein relate to a novel and distinct *Petunia-Calibrachoa* designated SAKPXC038, and to the seeds, plant parts, and tissue culture produced by that *Petunia-Calibrachoa* variety. All publications cited in this application are herein incorporated by reference.

*Petunia* and *Calibrachoa* are closely related. In the 1990's, several species of *Petunia* were crossed with *Calibrachoa*. The resulting hybrid offspring was named Petchoa.

The foregoing examples of the related art and limitations related therewith are intended to be illustrative and not exclusive. Other limitations of the related art will become apparent to those of skill in the art upon a reading of the specification.

SUMMARY

The following embodiments and aspects thereof are described in conjunction with systems, tools, and methods which are meant to be exemplary, not limiting in scope.

According to one embodiment, there is provided a *Petunia-Calibrachoa* plant which is valued as breeding line enabling the development of superior ornamental *Petunia-Calibrachoa* plants.

Another embodiment discloses a *Petunia-Calibrachoa* plant, wherein a sample of representative sample of plant tissue of said *Petunia-Calibrachoa* is deposited with a Budapest Depository.

Another embodiment relates to a plant, or a part thereof, produced by growing *Petunia-Calibrachoa* SAKPXC038, wherein the plant part comprises at least one cell of *Petunia-Calibrachoa* SAKPXC038.

Another embodiment relates to tissue culture produced from protoplasts or cells from the *Petunia-Calibrachoa* plants disclosed in the subject application, wherein said cells or protoplasts are produced from a plant part selected from the group consisting of pollen, ovules, embryos, protoplasts, meristematic cells, callus, pollen, leaves, ovules, anthers, cotyledons, hypocotyl, pistils, roots, root tips, flowers, seeds, petiole, and stems.

Another embodiment relates to a tissue or cell culture of regenerable cells produced from the plant of SAKPXC038 and a *Petunia-Calibrachoa* plant regenerated from the tissue or cell culture of SAKPXC038.

Another embodiment relates to a method of vegetatively propagating the plant of SAKPXC038, comprising the steps of: collecting tissue or cells capable of being propagated from a plant of SAKPXC038; cultivating said tissue or cells to obtain proliferated shoots; and rooting said proliferated shoots to obtain rooted plantlets; or cultivating said tissue or cells to obtain proliferated shoots, or to obtain plantlets and a plant produced by growing the plantlets or proliferated shoots of said plant.

A further embodiment relates to a method for producing an embryo or seed, wherein the method comprises crossing a SAKPXC038 plant with another plant and harvesting the resultant embryo or seed.

A further embodiment relates to a method for developing a *Petunia-Calibrachoa* plant in a *Petunia-Calibrachoa* plant breeding program, comprising applying plant breeding techniques comprising crossing, recurrent selection, mutation breeding, wherein said mutation breeding selects for a mutation that is spontaneous or artificially induced, backcrossing, pedigree breeding, marker enhanced selection, haploid/double haploid production, or transformation to the *Petunia-Calibrachoa* plant of SAKPXC038, or its parts, wherein application of said techniques results in development of a *Petunia-Calibrachoa* plant.

A further embodiment relates to a method of introducing a mutation into the genome of *Petunia-Calibrachoa* plant SAKPXC038, said method comprising mutagenesis of the plant, or plant part thereof, of SAKPXC038, wherein said mutagenesis is selected from the group consisting of temperature, long-term seed storage, tissue culture conditions, ionizing radiation, chemical mutagens, and targeting induced local lesions in genomes, and wherein the resulting plant comprises at least one genome mutation and producing plants therefrom.

A further embodiment relates to a method of editing the genome of *Petunia-Calibrachoa* plant SAKPXC038, wherein said method is selected from the group comprising zinc finger nucleases, transcription activator-like effector nucleases (TALENs), engineered homing endonucleases/meganucleases, and the clustered regularly interspaced short palindromic repeat (CRISPR)-associated protein9 (Cas9) system, and plants produced therefrom.

A further embodiment relates to a *Petunia-Calibrachoa* seed produced by growing SAKPXC038.

A further embodiment relates to a method of producing a *Petunia-Calibrachoa* plant, or part thereof, by growing a seed produced on SAKPXC038.

In addition to the exemplary aspects and embodiments described above, further aspects and embodiments will become apparent by study of the following descriptions.

DETAILED DESCRIPTION

The present invention comprises of a new and distinct cultivar of *Petunia-Calibrachoa* (Petchoa) referred to by the variety name SAKPXC038. Variety SAKPXC038 originated from a mutation of 'SAKPXC023' (U.S. Pat. No. 10,499,606) discovered in Marslev, Denmark in April 2020. 'SAKPXC023' has a wine-red flower color and a semi mounding habit.

In April 2020, the breeder discovered a plant from a group of plants that exhibited a rose star patterned flower color that was well blooming and had a semi-mounding plant habit. The line was given the experimental name 'D2021-PX411'. In December 2020, the selection was vegetatively propagated to produce rooted cuttings and plants of the selection were cultivated evaluated in an open field. In August 2021, the breeder observed the selected line to have its distinct characteristics remain stable. In March 2021, the selection was propagated again, and plants were cultivated. In August 2022, the breeder confirmed that the distinct characteristics of the selection were fixed and stable. Breeding work was conducted at Odense Research Station in Marslev, Denmark until December 2021, and beginning March 2022 it was processed at Kakegawa Research Station in Kakegawa, Japan. The selection was named SAKPXC038.

*Petunia-Calibrachoa* variety SAKPXC038 was grown under the following environmental conditions for plant growth: The terminal 1.0 to 1.5 inches of an actively growing stem was excised. The vegetative cuttings were propagated in five to six weeks. The base of the cuttings were dipped for 1 to 2 seconds in a 1:9 solution of DIP 'N GROW (1 solution: 9 water), a root inducing solution, immediately prior to sticking into the cell trays. Cuttings were stuck into plastic cell trays having 98 cells, and containing a moistened peat moss-based growing medium.

For the first week, the cuttings were misted with water from overhead for 10 seconds every 30 minutes until sufficient roots were formed.

Rooted cuttings were transplanted and grown in 20 cm diameter plastic pots in a glass greenhouse located in Salinas, California. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

*Petunia-Calibrachoa* variety SAKPXC038 has shown uniformity and stability, as described in the following variety description information. *Petunia-Calibrachoa* variety SAKPXC038 was tested for uniformity and stability a sufficient number of generations with careful attention to uniformity of plant type and has been increased with continued observation for uniformity.

*Petunia-Calibrachoa* variety SAKPXC038 has the following morphologic and other characteristics based primarily on data collected in Salinas, California, in September 2023. Plants were approximately five months from transplant into gallon pots from rooted cuttings, pinched once during growth under greenhouse conditions. Color references are to The R.H.S. Colour Chart of The Royal Horticultural Society of London (R.H.S.), 6th edition (2015). Anatomic labels are from *The Cambridge Illustrated Glossary of Botanical Terms*, by M. Hickey and C. King, Cambridge University.

TABLE 1

VARIETY DESCRIPTION INFORMATION

| Characteristic | SAKPXC038 |
|---|---|
| Form | Annual or Tender Perennial |
| Habit | Upright to Spreading |
| Height | 30.0 cm |
| Spread | 27.0 cm |
| Time to produce a rooted cutting | 4 weeks |
| Time to bloom from asexual propagation | 6 to 8 weeks |
| Stem description | Pliable; circular in cross-section |
| Number of branches | 4 |
| Stem diameter | 3.0 cm |
| Stem length | 20.0 cm |
| Stem color | 143A (Strong Yellow Green) |
| Stem anthocyanin | N/A |
| Stem internode length | 2.0 cm |
| Stem pubescence and color | Moderate NN155D (White) |
| Leaf arrangement | Alternate |
| Leaf shape | Elliptic |
| Leaf apex | Acute |
| Leaf base | Attenuate |
| Leaf margin | Entire |
| Leaf attachment | Sessile |
| Leaf texture (both surfaces) | Sticky |
| Leaf pubescence and color | Moderate NN155D (White) |
| Leaf venation | Pinnate |
| Leaf venation color | Upper: 144A (Strong Yellow Green)<br>Lower: 144B (Strong Yellow Green) |
| Leaf length | 2.6 cm |
| Leaf width | 1.0 cm |
| Leaf color | Upper: 146A (Moderate Olive Green)<br>Lower: 146B (Moderate Yellow Green) |
| Leaf fragrance | N/A |
| Petiole Color | NN155A (Yellowish White) |
| Petiole Length | 2.0 mm |
| Petiole Width | 2.0 mm |
| Flowering habit and type | Indeterminate, solitary |
| Total number of flowers at time of evaluation | 21 |
| Number of flowers per node | 1-2 in bloom |
| Flowering requirements | Will flower so long as day length is greater than 12 hours and temperature exceeds 13° C. |
| Duration of flower life | 5 days |
| Flower fragrance | Absent |
| Flower depth | 1.2 cm |
| Flower diameter | 6.5 cm |
| Corolla shape | Funnel shaped with five fused petals |
| Corolla tube length | 2.5 cm |
| Corolla tube diameter | 1.0 cm |
| Corolla tube pubescence and color | Descr. Outside of tube<br>Color: NN155D (White) |
| Flower bud shape | Cylindrical |
| Flower bud length | 3.7 cm |
| Flower bud diameter | .5 cm |
| Flower bud surface texture | Moderately pubescent |
| Flower bud color | N79B (Dark Purplish Red) |
| Peduncle length | 2.0 cm |
| Peduncle diameter | 2.0 mm |
| Peduncle pubescence and color | Moderate NN155D (White) |
| Peduncle color | 143B (Strong Yellow Green) with N77A (Greyish Purple) anthocyanin |
| Calyx description | Composed of 5 sepals, free |
| Sepal shape | Elliptical |
| Sepal attachment | Sessile |
| Sepal apex | Obtuse |
| Sepal base | Attenuate |
| Sepal margin | Entire |
| Sepal length | 1.8 cm |
| Sepal width | 3.0 mm |
| Sepal color | Upper: 144B (Strong Yellow Green)<br>Lower: 144A (Strong Yellow Green) |
| Petal shape | Obcordate |
| Petal length | 4.0 cm |
| Petal width | 3.8 cm |
| Petal apex | Abruptly acute; cuspidate |
| Petal margin | Entire |
| Petal texture (both surfaces) | Smooth |
| Petal color, upper surface | 61A (Deep Purplish Red) and NN78A (Strong Reddish Purple) along the fused parts of the corolla lobes |
| Petal color, lower surface | 70A (Moderate Purplish Red) |
| Young Flower RHS Color | 71A (Deep Purplish Red) |
| Aged Flower RHS Color | 71B (Strong Purplish Red) |
| Corolla tube color, inner surface | 14A (Vivid Yellow) |
| Corolla tube color, outer surface | 144D (Light Yellow Green) |
| Flower tube pubescence | Inner: absent<br>Outer: present, NN155D (White) |
| Stamen description, number, and length | Descr.: 5, free, arranged adjacent to pistil<br>Length: 2.0 cm |
| Filament color | Color: NN155C (White)<br>Length: 2.1 cm |
| Anther color and length | Color: Closest to 162C (Light Yellow)<br>Length: 1.0 mm |
| Pollen color and description | Powdery 150C (Brilliant Yellow Green) |
| Ovary description | Superior |
| Pistil description and length | 1 (per inflorescence);<br>Length: 1.8 cm |
| Stigma color and length | Color: 146A (Moderate Olive Green) and N92A (Dark Greyish Purple)<br>Length: 1.5 mm |
| Style color and length | 145C (Light Yellow Green); 1.6 cm |
| Fruit/seed set | None Observed |

SAKPXC038 is a new and unique variety of intergeneric *Calibrachoa-Petunia* owing to its rose star patterned flower color and semi-mounding plant growth habit. SAKPXC038 is most similar to the commercial *Calibrachoa-Petunia* variety 'SAKPXC026' (U.S. Pat. No. 10,492,458), commercially known as 'SuperCal® Lavender Star'; however there are differences in the flower color as described in the table below (color references are to the Royal Horticultural Society Colour Chart, 6$^{th}$ edition):

TABLE 2

| COMPARISON WITH SIMILAR VARIETY | | |
|---|---|---|
| Characteristic | SAKPXC038 | SAKPXC026 |
| Petal color, upper surface | 61A (Deep Purplish Red) and NN78A (Strong Reddish Purple) along the fused parts of the corolla lobes | RHS N74C (Red-Purple) on mature flowers with RHS 155C (White) star pattern and subtle RHS 152B (Yellow-Green) midveins |
| Petal color, lower surface | 70A (Moderate Purplish Red) | RHS 75B (Light Purple) lightening to RHS 75D (Very Pale Purple) near center with RHS N144C (Strong Yellow Green) veins |
| Flower diameter | 6.5 cm | 5.0 cm |

SAKPXC038 differs from the parental line as described in Table 3.

TABLE 3

| COMPARISON WITH PARENTAL LINE | | |
|---|---|---|
| Characteristic | SAKPXC038 | SAKPXC023 |
| Petal color, upper surface | 61A (Deep Purplish Red) and NN78A (Strong Reddish Purple) along the fused parts of the corolla lobes | Closest to but brighter than RHS 59A (Red - Purple) with RHS N77A (Purple) at mid - vein |
| Flower diameter | 6.5 cm | 7.4 cm |

Further Embodiments

Breeding with *Petunia-Calibrachoa* Variety SAKPXC038

The complexity of inheritance influences choice of the breeding method. Backcross breeding is used to transfer one or a few favorable genes for a highly heritable trait into a desirable variety. This approach has been used extensively for breeding disease-resistant varieties. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Promising advanced breeding varieties are thoroughly tested and compared to appropriate standards in environments representative of the commercial target area(s) for three or more years. The best varieties are candidates for new commercial varieties; those still deficient in a few traits may be used as parents to produce new populations for further selection.

These processes, which lead to the final step of marketing and distribution, are time-consuming and require precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard variety. If a single observation is inconclusive, replicated observations provide a better estimate of its genetic worth.

The goal of *Petunia-Calibrachoa* breeding is to develop new and superior *Petunia-Calibrachoa* varieties and hybrids. The breeder initially selects and crosses two or more parental varieties, followed by repeated selfing and selection, producing many new genetic combinations. The breeder can theoretically generate billions of different genetic combinations via crossing, selection, selfing, and mutations.

Using *Petunia-Calibrachoa* Variety SAKPXC038 to Develop Other *Petunia-Calibrachoa* Varieties

*Petunia-Calibrachoa* varieties such as *Petunia-Calibrachoa* variety SAKPXC038 are a source of breeding material that may be used to develop new *Petunia-Calibrachoa* varieties. Plant breeding techniques known in the art and used in a *Petunia-Calibrachoa* breeding program include, but are not limited to, recurrent selection, mass selection, bulk selection, mass selection, backcrossing, pedigree breeding, open pollination breeding, restriction fragment length polymorphism enhanced selection, genetic marker enhanced selection, making double haploids, transformation, and gene editing. These techniques can be used singularly or in combinations. There are many analytical methods available to evaluate a new variety. The oldest and most traditional method of analysis is the observation of phenotypic traits, but genotypic analysis may also be used.

Additional Breeding Methods

Any plants produced using the SAKPXC038 plants disclosed in the present application as at least one parent are also an embodiment. These methods are well-known in the art and some of the more commonly used breeding methods are described herein. Descriptions of breeding methods can be found in one of several reference books (e.g., Allard, "Principles of Plant Breeding" (1999); and Vainstein, "Breeding for Ornamentals: Classical and Molecular Approaches," Kluwer Academic Publishers (2002); Callaway, "Breeding Ornamental Plants," Timber Press (2000).

Breeding steps that may be used in the *Petunia-Calibrachoa* variety SAKPXC038 plant breeding program can include for example, pedigree breeding, backcrossing, mutation breeding, and recurrent selection. In conjunction with these steps, techniques such as RFLP-enhanced selection, genetic marker enhanced selection (for example, SSR markers), Gene Editing and the making of double haploids may be utilized.

As used herein, the term "plant" or plant part includes plant cells, plant protoplasts, plant cell tissue cultures from which SAKPXC038 plants can be regenerated, plant calli, plant clumps, and plant cells that are intact in plants or parts of plants, such as pollen, ovules, embryos, protoplasts, meristematic cells, callus, pollen, leaves, ovules, anthers, cotyledons, hypocotyl, pistils, roots, root tips, seeds, flowers, petiole, pods, shoot, or stems and the like.

Pedigree Breeding

Pedigree breeding starts with the crossing of two genotypes, such as *Petunia-Calibrachoa* variety SAKPXC038 and another *Petunia-Calibrachoa* variety having one or more desirable characteristics that is lacking or which complements *Petunia-Calibrachoa* variety SAKPXC038. If the two original parents do not provide all the desired characteristics, other sources can be included in the breeding population. In the pedigree method, superior plants are selfed and selected in successive filial generations. In the succeeding filial generations, the heterozygous condition gives way to homogeneous varieties as a result of self-pollination and selection.

Typically, in the pedigree method of breeding, five or more successive filial generations of selfing and selection is practiced: $F_1$ to $F_2$; $F_2$ to $F_3$; $F_3$ to $F_4$; $F_4$ to $F_5$; etc. After a sufficient amount of inbreeding, successive filial generations will serve to increase seed of the developed variety. Preferably, the developed variety comprises homozygous alleles at about 95% or more of its loci.

Backcross Breeding

Backcross breeding has been used to transfer genes for a simply inherited, highly heritable trait into a desirable homozygous variety or inbred variety which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have the attributes of the recurrent parent (e.g., variety) and the desirable trait transferred from the donor parent. This is also known as single gene conversion and/or backcross conversion.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good commercial characteristics yet lacks that desirable trait or traits. However, the same procedure can be used to move the progeny toward the genotype of the recurrent parent, but at the same time retain many components of the nonrecurrent parent by stopping the backcrossing at an early stage and proceeding with selfing and selection. As used herein, progeny refers to the descendants of one or more of the parental lines and includes an $F_1$ *Petunia-Calibrachoa* plant produced from the cross of two *Petunia-Calibrachoa* plants where at least one plant includes a *Petunia-Calibrachoa* plant disclosed herein and progeny further includes, but is not limited to, subsequent $F_2$, $F_3$, $F_4$, $F_5$, $F_6$, $F_7$, $F_8$, $F_9$, and $F_{10}$ generational crosses with the recurrent parental line. For example, a *Petunia-Calibrachoa* plant may be crossed with another variety to produce a first-generation progeny plant. The first-generation progeny plant may then be backcrossed to one of its parent varieties to create a $BC_1$ or $BC_2$. Progeny are selfed and selected so that the newly developed variety has many of the attributes of the recurrent parent and yet several of the desired attributes of the nonrecurrent parent. This approach leverages the value and strengths of the recurrent parent for use in new *Petunia-Calibrachoa* varieties.

Therefore, another embodiment is a method of making a backcross conversion of *Petunia-Calibrachoa* variety SAKPXC038, comprising the steps of crossing *Petunia-Calibrachoa* variety SAKPXC038 with a donor plant comprising a desired trait, selecting an $F_1$ progeny plant comprising the desired trait, and backcrossing the selected $F_1$ progeny plant to *Petunia-Calibrachoa* variety SAKPXC038. This method may further comprise the step of obtaining a molecular marker profile of *Petunia-Calibrachoa* variety SAKPXC038 and using the molecular marker profile to select for a progeny plant with the desired trait and the molecular marker profile of *Petunia-Calibrachoa* variety SAKPXC038.

Recurrent Selection and Mass Selection

Recurrent selection is a method used in a plant breeding program to improve a population of plants. *Petunia-Calibrachoa* variety SAKPXC038 is suitable for use in a recurrent selection program. The method entails individual plants cross pollinating with each other to form progeny. The progeny are grown and the superior progeny selected by any number of selection methods, which include individual plant, half-sib progeny, full-sib progeny, and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic variety. A synthetic variety is the resultant progeny formed by the intercrossing of several selected varieties.

Mass selection is a useful technique when used in conjunction with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk, and then using a sample of the seed harvested in bulk to plant the next generation. Also, instead of self-pollination, directed pollination could be used as part of the breeding program.

Mass and recurrent selections can be used to improve populations of either self- or cross-pollinating crops. A genetically variable population of heterozygous individuals is either identified, or created, by intercrossing several different parents. The plants are selected based on individual superiority, outstanding progeny, or excellent combining ability. The selected plants are intercrossed to produce a new population in which further cycles of selection are continued.

Protoplast Fusion

Also known as somatic fusion, this process can be used with SAKPXC038 to create hybrids. The resulting hybrid plants have the chromosomes of each parent and thus the process is useful for incorporating new traits. The protoplast fusion technique is well known in the art; see for example Hamill J. D., Cocking E. C. (1988) Somatic Hybridization of Plants and its Use in Agriculture. In: Pais M. S. S., Mavituna F., Novais J. M. (eds) Plant Cell Biotechnology. NATO ASI Series (Series H: Cell Biology), vol 18.

Mutation Breeding

Mutation breeding is another method of introducing new traits into *Petunia-Calibrachoa* variety SAKPXC038. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, ionizing radiation, such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm); chemical mutagens (such as base analogues (5-bromo-uracil)), related compounds (8-ethoxy caffeine), antibiotics (streptonigrin), alkylating agents (sulfur mustards, nitrogen mustards, epoxides, ethylenamines, sulfates, sulfonates such as ethyl methanesulfonate, sulfones, lactones), sodium azide, hydroxylamine, nitrous acid, methylnitrilsourea, or acridines; TILLING (targeting induced local lesions in genomes), where mutation is induced by chemical mutagens and mutagenesis is accompanied by the isolation of chromosomal DNA from every mutated plant line or seed and screening of the population of the seed or plants is performed at the DNA level using advanced molecular techniques. Once a desired trait is observed through mutagenesis the trait may then be incorporated into existing germplasm by traditional breeding techniques. Details of mutation breeding can be found in Vainstein, "Breeding for Ornamentals: Classical and Molecular Approaches," Kluwer Academic Publishers (2002); Sikora, Per, et al., "Mutagenesis as a Tool in Plant Genetics, Functional Genomics, and Breeding" *International Journal of Plant Genomics.* 2011 (2011); 13 pages. In addition, mutations created in other *Petunia-Calibrachoa* plants may be used to produce a backcross conversion of *Petunia-Calibrachoa* that comprises such mutation.

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformant plants obtained with the protoplasm of the embodiments are intended to be within the scope of the embodiments.

Gene Editing Using CRISPR

Targeted gene editing can be done using CRISPR/Cas9 technology (Saunders & Joung, Nature Biotechnology, 32, 347-355, 2014). CRISPR is a type of genome editing system that stands for Clustered Regularly Interspaced Short Palindromic Repeats. This system and CRISPR-associated (Cas) genes enable organisms, such as select bacteria and archaea, to respond to and eliminate invading genetic material. Ishino, Y., et al. *J. Bacteriol.* 169, 5429-5433 (1987). These repeats were known as early as the 1980s in *E. coli*, but Barrangou and colleagues demonstrated that *S. thermophilus* can acquire resistance against a bacteriophage by integrating a fragment of a genome of an infectious virus into its CRISPR locus. Barrangou, R., et al. *Science* 315, 1709-1712 (2007). Many plants have already been modified using the CRISPR system, including *Petunia*. See for example, Zhang, B. et al., "Exploiting the CRISPR/Cas9 System for Targeted Genome Mutagenesis in *Petunia*" *Science Reports*, Vol. 6, February 2016.

Gene editing can also be done using crRNA-guided surveillance systems for gene editing. Additional information about crRNA-guided surveillance complex systems for gene editing can be found in the following documents, which are incorporated by reference in their entirety: U.S. Application Publication No. 2010/0076057 (Sontheimer et al., Target DNA Interference with crRNA); U.S. Application Publication No. 2014/0179006 (Feng, CRISPR-CAS Component Systems, Methods, and Compositions for Sequence Manipulation); U.S. Application Publication No. 2014/0294773 (Brouns et al., Modified Cascade Ribonucleoproteins and Uses Thereof); Sorek et al., *Annu. Rev. Biochem.* 82:273-266, 2013; and Wang, S. et al., *Plant Cell Rep* (2015) 34:1473-1476.

Therefore, it is another embodiment to use the CRISPR system on *Petunia-Calibrachoa* variety SAKPXC038 to modify traits and resistances or tolerances to pests, herbicides, and viruses.

Gene Editing Using TALENs

Transcription activator-like effector nucleases (TALENs) have been successfully used to introduce targeted mutations via repair of double stranded breaks (DSBs) either through non-homologous end joining (NHEJ), or by homology-directed repair (HDR) and homology-independent repair in the presence of a donor template. Thus, TALENs are another mechanism for targeted genome editing using SAKPXC038. The technique is well known in the art; see for example Malzahn, Aimee et al. "Plant genome editing with TALEN and CRISPR" Cell & bioscience vol. 7 21. 24 Apr. 2017.

Therefore, it is another embodiment to use the TALENs system on *Petunia-Calibrachoa* variety SAKPXC038 to modify traits and resistances or tolerances to pests, herbicides, and viruses.

Other Methods of Genome Editing

In addition to CRISPR and TALENs, two other types of engineered nucleases can be used for genome editing: engineered homing endonucleases/meganucleases (EMNs), and zinc finger nucleases (ZFNs). These methods are well known in the art. See for example, Petilino, Joseph F. "Genome editing in plants via designed zinc finger nucleases" *In Vitro Cell Dev Biol Plant.* 51(1): pp. 1-8 (2015); and Daboussi, Fayza, et al. "Engineering Meganuclease for Precise Plant Genome Modification" in Advances in New Technology for Targeted Modification of Plant Genomes. Springer Science+Business. pp 21-38 (2015).

Therefore, it is another embodiment to use engineered nucleases on *Petunia-Calibrachoa* variety SAKPXC038 to modify traits and resistances or tolerances to pests, herbicides, and viruses.

Introduction of a New Trait or Locus into *Petunia-Calibrachoa* Variety SAKPXC038

*Petunia-Calibrachoa* variety SAKPXC038 represents a new variety into which a new locus or trait may be introgressed. Direct transformation and backcrossing represent two important methods that can be used to accomplish such an introgression. The term backcross conversion and single locus conversion are used interchangeably to designate the product of a backcrossing program.

Molecular Techniques Using *Petunia-Calibrachoa* Variety SAKPXC038

The advent of new molecular biological techniques has allowed the isolation and characterization of genetic elements with specific functions. Traditional plant breeding has principally been the source of new germplasm, however, advances in molecular technologies have allowed breeders to provide varieties with novel and much wanted commercial attributes. Molecular techniques such as transformation are popular in breeding ornamental plants and well-known in the art. See Vainstein, "Breeding for Ornamentals: Classical and Molecular Approaches," Kluwer Academic Publishers (2002).

Breeding with Molecular Markers

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses. Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), and Single Nucleotide Polymorphisms (SNPs), may be used in plant breeding methods utilizing *Petunia-Calibrachoa* variety SAKPXC038. See Vainstein, "Breeding for Ornamentals: Classical and Molecular Approaches," Kluwer Academic Publishers (2002).

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome. See for example, Fletcher, Richard S., et al., "QTL analysis of root morphology, flowering time, and yield reveals trade-offs in response to drought in *Brassica napus Journal of Experimental Biology.* 66 (1): 245-256 (2014). QTL markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Production of Double Haploids

The production of double haploids can also be used for the development of plants with a homozygous phenotype in the breeding program. For example, a *Petunia-Calibrachoa* plant for which *Petunia-Calibrachoa* variety SAKPXC038 is a parent can be used to produce double haploid plants. Double haploids are produced by the doubling of a set of chromosomes (IN) from a heterozygous plant to produce a completely homozygous individual. This can be advantageous because the process omits the generations of selfing needed to obtain a homozygous plant from a heterozygous source. For example, see, Ferric, Alison M. R., et al., "Review of Doubled Haploidy Methodologies in Ornamental Species" *Propagation of Ornamental Plants.* 11(2): pp. 63-77 (2011).

Thus, an embodiment is a process for making a substantially homozygous *Petunia-Calibrachoa* variety SAKPXC038 progeny plant by producing or obtaining a seed from the cross of *Petunia-Calibrachoa* variety SAKPXC038 and another *Petunia-Calibrachoa* plant and applying double haploid methods to the $F_1$ seed or $F_1$ plant or to any successive filial generation.

In particular, a process of making seed retaining the molecular marker profile of *Petunia-Calibrachoa* variety SAKPXC038 is contemplated, such process comprising obtaining or producing $F_1$ seed for which *Petunia-Calibrachoa* variety SAKPXC038 is a parent, inducing doubled haploids to create progeny without the occurrence of meiotic segregation, obtaining the molecular marker profile of *Petunia-Calibrachoa* variety SAKPXC038, and selecting progeny that retain the molecular marker profile of *Petunia-Calibrachoa* variety SAKPXC038.

Expression Vectors for *Petunia-Calibrachoa* Transformation: Marker Genes

Plant transformation involves the construction of an expression vector which will function in plant cells. Such a vector comprises DNA comprising a gene under control of, or operatively linked to, a regulatory element (for example, a promoter). Expression vectors include at least one genetic marker operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well-known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Another commonly used selectable marker gene is the hygromycin phosphotransferase gene which confers resistance to the antibiotic hygromycin.

Selectable marker genes for plant transformation not of bacterial origin include, for example, mouse dihydrofolate reductase, plant 5-enolpyruvylshikimate-3-phosphate synthase, and plant acetolactate synthase (Eichholtz, et al., *Somatic Cell Mol. Genet.,* 13:67 (1987); Shah, et al., *Science,* 233:478 (1986); Charest, et al., *Plant Cell Rep.,* 8:643 (1990)).

Another class of marker genes for plant transformation requires screening of presumptively transformed plant cells, rather than direct genetic selection of transformed cells, for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used marker genes for screening presumptively transformed cells include β-glucuronidase (GUS), β-galactosidase, luciferase, and chloramphenicol acetyltransferase (Jefferson, R. A., *Plant Mol. Biol. Rep.,* 5:387 (1987); Teeri, et al., *EMBO J.,* 8:343 (1989); Koncz, et al., *Proc. Natl. Acad. Sci. USA,* 84:131 (1987); DeBlock, et al., *EMBO J.,* 3:1681 (1984)).

Expression Vectors for *Petunia-Calibrachoa* Transformation: Promoters

Genes included in expression vectors must be driven by a nucleotide sequence comprising a regulatory element (for example, a promoter). Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in a certain tissue are referred to as "tissue-specific." A "cell-type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell-type specific, and inducible promoters constitute the class of "non-constitutive" promoters. A "constitutive" promoter is a promoter that is active under most environmental conditions. Many types of promoters are well known in the art.

Signal Sequences for Targeting Proteins to Subcellular Compartments

Transport of a protein produced by transgenes to a subcellular compartment, such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized. Many signal sequences are well-known in the art. See, for example, Becker, et al., *Plant Mol. Biol.,* 20:49 (1992); Knox, C., et al., *Plant Mol. Biol.,* 9:3-17 (1987); Lerner, et al., *Plant Physiol.,* 91:124-129 (1989); Frontes, et al., *Plant Cell,* 3:483-496 (1991); Matsuoka, et al., *Proc. Natl. Acad. Sci.,* 88:834 (1991); Gould, et al., *J. Cell. Biol.,* 108:1657 (1989); Creissen, et al., *Plant J.,* 2:129 (1991); Kalderon, et al., *Cell,* 39:499-509 (1984); Steifel, et al., *Plant Cell,* 2:785-793 (1990).

Foreign Protein Genes: Transformation

Various promoters, targeting sequences, enhancing sequences, and other DNA sequences can be inserted into the genome for the purpose of altering the expression of genes.

Many techniques for altering gene expression are well-known to one of skill in the art, including, but not limited to, knock-outs (such as by insertion of a transposable element such as Mu (Vicki Chandler, *The Maize Handbook*, Ch. 118 (Springer-Verlag 1994)) or other genetic elements such as a FRT, Lox, or other site specific integration sites; antisense technology (see, e.g., Sheehy, et al., *PNAS USA,* 85:8805-8809 (1988) and U.S. Pat. Nos. 5,107,065, 5,453,566, and 5,759,829); co-suppression (e.g., Taylor, *Plant Cell,* 9:1245 (1997); Jorgensen, *Trends Biotech.,* 8 (12): 340-344 (1990); Flavell, *PNAS USA,* 91:3490-3496 (1994); Finnegan, et al., *Bio/Technology,* 12:883-888 (1994); Neuhuber, et al., *Mol. Gen. Genet.,* 244:230-241 (1994)); RNA interference (Napoli, et al., *Plant Cell,* 2:279-289 (1990); U.S. Pat. No. 5,034,323; Sharp, *Genes Dev.,* 13:139-141 (1999); Zamore, et al., *Cell,* 101:25-33 (2000); Montgomery, et al., *PNAS USA,* 95:15502-15507 (1998)), virus-induced gene silencing (Burton, et al., *Plant Cell,* 12:691-705 (2000); Baulcombe, *Curr. Op. Plant Bio.,* 2:109-113 (1999)); target-RNA-specific ribozymes (Haseloff, et al., *Nature,* 334:585-591 (1988)); hairpin structures (Smith, et al., *Nature,* 407:319-320 (2000); U.S. Pat. Nos. 6,423,885, 7,138,565, 6,753, 139, and 7,713,715); MicroRNA (Aukerman & Sakai, *Plant Cell,* 15:2730-2741 (2003)); ribozymes (Steinecke, et al., *EMBO J.,* 11:1525 (1992); Perriman, et al., *Antisense Res. Dev.,* 3:253 (1993)); oligonucleotide mediated targeted modification (e.g., U.S. Pat. Nos. 6,528,700 and 6,911,575); Zn-finger targeted molecules (e.g., U.S. Pat. Nos. 7,151,201, 6,453,242, 6,785,613, 7,177,766 and 7,788,044); transposable elements (e.g. Dubin, M. J., et al., Transposons: a blessing curse, Current opinion in plant biology, Vol: 42, Page: 23-29, 2018 and Eric T. Johnson, Jesse B. Owens & Stefan Moisyadi (2016) Vast potential for using the piggyBac transposon to engineer transgenic plants at specific genomic locations, Bioengineered, 7:1, 3-6) and other methods or combinations of the above methods known to those of skill in the art.

The foregoing methods for transformation may be used for producing a transgenic variety. The transgenic variety could then be crossed with another (non-transformed or transformed) variety in order to produce a new transgenic variety. Alternatively, a genetic trait that has been engineered into a particular *Petunia-Calibrachoa* variety using the foregoing transformation techniques could be moved into another variety using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene. As used herein, "crossing" can refer to a simple x by y cross or the process of backcrossing depending on the context.

Likewise, by means of one embodiment, genes can be expressed in transformed plants. More particularly, plants can be genetically engineered to express various phenotypes of interest, including, but not limited to, genes that confer resistance to pests or disease, genes that confer resistance to an herbicide, genes that confer or contribute to a value-added or desired trait, genes that control male sterility, genes that create a site for site specific DNA integration, and genes that affect abiotic stress resistance. Many hundreds if not thousands of different genes are known and could potentially be introduced into a plant according to the invention. Non-limiting examples of particular genes and corresponding phenotypes one may choose to introduce into a plant include one or more genes for insect tolerance, such as a *Bacillus thuringiensis* (Bt.) gene, pest tolerance such as genes for fungal disease control, herbicide tolerance such as genes conferring glyphosate tolerance, and genes for quality improvements such as, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference in their entirety. In another embodiment, the structural gene can confer tolerance to the herbicide glyphosate as conferred by genes including, but not limited to *Agrobacterium* strain CP4 glyphosate resistant EPSPS gene (aroA: CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety. Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., *Biotech. Gen. Engin. Rev.,* 9:207, 1991). The RNA could also be a catalytic RNA molecule (i.e., a ribozyme) engineered to cleave a desired endogenous mRNA product (see for example, Gibson and Shillito, *Mol. Biotech.,* 7:125, 1997). Thus, any gene which produces a protein or mRNA which expresses a phenotype or morphology change of interest is useful for the practice of one or more embodiments.

Tissue Culture

Further reproduction of the variety can occur by tissue culture and regeneration. Tissue culture of various tissues of ornamental plants and *Petunia-Calibrachoa* SAKPXC038 and regeneration of plants therefrom is well-known and widely published. For example, reference may be had to Valla Rego, Luciana et al., Crop Breeding and Applied Technology. 1 (3): 283-300 (2001); Komatsuda, T., et al., *Crop Sci.,* 31:333-337 (1991); Stephens, P. A., et al., *Theor. Appl. Genet.,* 82:633-635 (1991); Komatsuda, T., et al., *Plant Cell, Tissue and Organ Culture,* 28:103-113 (1992); Dhir, S., et al., *Plant Cell Reports,* 11:285-289 (1992); Pandey, P., et al., *Japan J. Breed.,* 42:1-5 (1992); and Shetty, K., et al., Plant *Science,* 81:245-251 (1992). Thus, another embodiment is to provide cells which upon growth and differentiation produce *Petunia-Calibrachoa* plants having the physiological and morphological characteristics of *Petunia-Calibrachoa* SAKPXC038 described in the present application.

Regeneration refers to the development of a plant from tissue culture. The term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, petioles, leaves, stems, roots, root tips, anthers, pistils, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques, the disclosures of which are incorporated herein by reference.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions, and sub-combinations as are within their true spirit and scope.

One or more aspects may be embodied in other specific forms without departing from its spirit or essential characteristics. The described embodiments are to be considered in all respects only as illustrative and not restrictive. The scope of the embodiments is, therefore, indicated by the appended claims rather than by the foregoing description. All changes which come within the meaning and range of equivalency of the claims are to be embraced within their scope.

The foregoing discussion of the embodiments has been presented for purposes of illustration and description. The foregoing is not intended to limit the embodiments to the form or forms disclosed herein. In the foregoing Detailed Description for example, various features of the embodiments are grouped together in one or more embodiments for the purpose of streamlining the disclosure. This method of disclosure is not to be interpreted as reflecting an intention that the claimed embodiments require more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment.

Moreover, though the description of the embodiments has included description of one or more embodiments and certain variations and modifications, other variations and modifications are within the scope of the embodiments (e.g., as may be within the skill and knowledge of those in the art, after understanding the present disclosure). It is intended to obtain rights which include alternative embodiments to the extent permitted, including alternate, interchangeable and/or equivalent structures, functions, ranges or acts to those claimed, whether or not such alternate, interchangeable and/or equivalent structures, functions, ranges or acts are disclosed herein, and without intending to publicly dedicate any patentable subject matter.

The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the embodiments unless otherwise claimed. No language in the specification should be construed as indicating any non-claimed element as essential to the practice of one or more embodiments.

Deposit Information

A plant tissue deposit of the Sakata Seed Corporation proprietary *petunia-calibrachoa* variety SAKPXC038 disclosed above and recited in the appended claims is maintained by Sakata Seed Corporation. A deposit was made on Sep. 13, 2024 with the Provasoli-Guillard National Center for Marine Algae and Microbiota, Bigelow Laboratory for Ocean Sciences, 60 Bigelow Drive, East Boothbay, Maine 04544, United States. The NCMA Accession No. is 202409012. Access to this deposit will be available during the pendency of this application to persons determined by the Commissioner of Patents and Trademarks to be entitled thereto under 37 C.F.R. 1.14 and 35 U.S.C. § 122. Upon allowance of any claims in this application, all restrictions on the availability to the public of the variety will be irrevocably removed by affording access to a deposit of the plant tissue deposit of the same variety with the Provasoli-Guillard National Center for Marine Algae and Microbiota, Bigelow Laboratory for Ocean Sciences. The deposit will be maintained in the depository for a period of 30 years, or 5 years after the last request, or for the effective life of the patent, whichever is longer, and will be replaced if necessary, during that period.

To satisfy the enablement requirements of 35 U.S.C. 112, and to certify that the deposit of the present disclosure meets the criteria set forth in 37 CFR 1.801-1.809 and Manual of Patent Examining Procedure (MPEP) 2402-2411.05, Applicants hereby make the following statements regarding the deposited *petunia-calibrachoa* variety SAKPXC038 (deposited as The NCMA No. 202409012).

If the deposit is made under the terms of the Budapest Treaty, the instant disclosure will be irrevocably and without restriction released to the public upon the granting of a patent.

If the deposit is made not under the terms of the Budapest Treaty, Applicant(s) provides assurance of compliance by following statements:

1. During the pendency of this application, access to the disclosure will be afforded to the Commissioner upon request;
2. All restrictions on availability to the public will be irrevocably removed upon granting of the patent under conditions specified in 37 CFR 1.808;
3. The deposit will be maintained in a public repository for a period of 30 years or 5 years after the last request or for the effective life of the patent, whichever is longer;
4. A test of the viability of the biological material at the time of deposit will be conducted by the public depository under 37 CFR 1.807; and The deposit will be replaced if it should ever become unavailable.

Access to this deposit will be available during the pendency of this application to persons determined by the Commissioner of Patents and Trademarks to be entitled thereto under 37 C.F.R. § 1.14 and 35 U.S.C. § 122. Upon granting of any claims in this application, all restrictions on the availability to the public of the variety will be irrevocably removed by affording access to a deposit with the NCMA.

What is claimed is:

1. A plant of *Petunia-Calibrachoa* variety SAKPXC038, wherein a representative sample of plant tissue of SAKPXC038 was deposited under NCMA Accession No. 202409012.

2. A plant or a plant part thereof produced by growing the plant of claim 1, wherein the plant part comprises a cell of a plant organ chosen from the group consisting of leaf, hypocotyl, meristem, root, root tip, pistil, anther, flower, and stem, and wherein the plant or plant part comprises at least one cell of *Petunia-Calibrachoa* variety SAKPXC038.

3. A *Petunia-Calibrachoa* plant, or part thereof, wherein said plant or part thereof has all of the physiological and morphological characteristics of the *Petunia-Calibrachoa* plant of claim 1.

4. A tissue or cell culture of regenerable cells produced from the plant of claim 1, wherein the tissue or cell culture of regenerable cells comprise all of the morphological and physiological characteristics of a cell or tissue of *petunia-calibrachoa* SAKPXC038.

5. The tissue or cell culture of claim 4, comprising tissues or cells from a plant organ or tissue type selected from the group consisting of leaf, hypocotyl, meristem, root, root tip, pistil, anther, flower and stem.

6. A *Petunia-Calibrachoa* plant regenerated from the tissue or cell culture of claim 5, wherein said plant has all of the morphological and physiological characteristics of *Petunia-Calibrachoa* SAKPXC038.

7. A method of vegetatively propagating the plant of claim 1, comprising the steps of: collecting tissue or cells capable of being propagated from said plant; cultivating said tissue or cells to obtain proliferated shoots; and rooting said proliferated shoots to obtain rooted plantlets; or cultivating said tissue or cells to obtain proliferated shoots, or to obtain plantlets.

8. An F1 *Petunia-Calibrachoa* plant produced by growing the plantlets or proliferated shoots of claim 7.

9. A method for producing an embryo or seed, wherein the method comprises crossing the plant of claim 1 with another plant and harvesting the resultant embryo or seed.

10. A method of determining the genotype of the *Petunia-Calibrachoa* plant of claim 1, wherein said method comprises obtaining a sample of nucleic acids from said plant and detecting in said nucleic acids a plurality of polymorphisms.

11. A method of producing a *Petunia-Calibrachoa* plant resistant to the group consisting of herbicides, insects, and disease, wherein the method comprises transforming the *Petunia-Calibrachoa* plant of claim 1 with a transgene, and wherein said transgene confers resistance to an herbicide, insecticide, or disease.

12. An herbicide, insect, or disease resistant plant produced by the method of claim 11, wherein said plant is herbicide, insect, or disease resistant and otherwise has all of the physiological and morphological characteristics of SAKPXC038.

13. A method for producing a *Petunia-Calibrachoa* plant, said method comprising: a) crossing two *Petunia-Calibrachoa* plants, b) harvesting the resultant *Petunia-Calibrachoa* seed, c) growing the seed from step b to produce progeny, and d) selecting resulting progeny; wherein at least one of the two *Petunia-Calibrachoa* plants is said SAKPXC038 of claim 1.

14. The method of claim 13, further comprising propagating the plant via seed, cutting, or tissue culture.

15. A method for producing a *Petunia-Calibrachoa* plant, said method comprising: propagating a vegetative cutting from a stock *Petunia-Calibrachoa* plant, thereby producing the *Petunia-Calibrachoa* plant; wherein the stock *Petunia-Calibrachoa* plant is a product of a single cross between: a parental line plant with another plant, or with itself; wherein the parental line plant is said SAKPXC038 of claim 1.

16. The method of claim 15, further comprising propagating the plant via seed, cutting, or tissue culture.

17. A method for producing a *Petunia-Calibrachoa* plant, said method comprising: propagating a vegetative cutting from a stock *Petunia-Calibrachoa* plant, thereby producing the *Petunia-Calibrachoa* plant wherein the stock *Petunia-Calibrachoa* plant is a product of applying a plant breeding technique to a *Petunia-Calibrachoa* parental line plant; wherein the parental line plant is said SAKPXC038 of claim 1.

18. The method of claim 17, further comprising propagating the plant via seed, cutting, or tissue culture.

19. The method of claim 17, wherein said plant breeding technique is selected from the group consisting of recurrent selection, mass selection, hybridization, open-pollination, backcrossing, pedigree breeding, marker enhanced selection, mutation breeding, wherein said mutation selected is spontaneous or artificially induced.

* * * * *